(12) United States Patent
Rosen et al.

(10) Patent No.: US 11,786,286 B2
(45) Date of Patent: *Oct. 17, 2023

(54) DERMATOLOGICAL CRYOSPRAY DEVICES HAVING LINEAR ARRAY OF NOZZLES AND METHODS OF USE

(71) Applicant: R2 Technologies, Inc., San Ramon, CA (US)

(72) Inventors: Jesse Rosen, Albany, CA (US); Erik Stauber, Albany, CA (US); Steven Harrington, Cardiff, CA (US); Ryan Richard Butrym, Cardiff by the Sea, CA (US)

(73) Assignee: R2 Technologies, Inc., San Ramon, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 17/245,744

(22) Filed: Apr. 30, 2021

(65) Prior Publication Data

US 2021/0244459 A1 Aug. 12, 2021

Related U.S. Application Data

(63) Continuation of application No. 16/020,852, filed on Jun. 27, 2018, now Pat. No. 11,013,547.

(Continued)

(51) Int. Cl.
*A61B 18/02* (2006.01)
*A61F 7/00* (2006.01)
(Continued)

(52) U.S. Cl.
CPC .......... *A61B 18/0218* (2013.01); *A61B 18/02* (2013.01); *A61F 7/0085* (2013.01);
(Continued)

(58) Field of Classification Search
CPC ................ A61B 18/02; A61B 18/0218; A61B 2018/00005; A61B 2018/00011;
(Continued)

(56) References Cited

U.S. PATENT DOCUMENTS 3,651,813 A 3/1972 Bryne
3,664,344 A 5/1972 Bryne
(Continued)

FOREIGN PATENT DOCUMENTS

CN 101257855 A 9/2008
CN 104394813 A 3/2015
(Continued)

OTHER PUBLICATIONS

Andrews, Cryosurgery for Common Skin Conditions, American Family Physician, vol. 69, Issue 10, May 15, 2004, pp. 2365-2372.
(Continued)

*Primary Examiner* — Thomas A Giuliani
(74) *Attorney, Agent, or Firm* — Kilpatrick Townsend & Stockton LLP

(57) ABSTRACT

The present invention is directed to improved systems, devices, and methods for delivery of a cryogen to the skin of a patient for skin treatment. A cryospray device configured to deliver a cryogen to a patient's skin can include an applicator, a supply channel, and a nozzle assembly. The applicator can include a head portion, and the supply channel can extend through at least a portion of the head portion. The nozzle assembly can be coupled to the head portion and can be fluidly coupled to the supply channel. The nozzle assembly can include a linear array of orifices that are configured to direct a planar spray of the cryogen to cool an area of a skin tissue of the patient in a linear cooling treatment.

24 Claims, 9 Drawing Sheets

Related U.S. Application Data

(60) Provisional application No. 62/527,652, filed on Jun. 30, 2017.

(51) Int. Cl.
    *A61B 18/00*         (2006.01)
    *A61B 17/00*         (2006.01)

(52) U.S. Cl.
    CPC ............... *A61B 2017/00747* (2013.01); *A61B 2018/00005* (2013.01); *A61B 2018/00041* (2013.01); *A61B 2018/00452* (2013.01); *A61B 2018/00458* (2013.01); *A61B 2018/00791* (2013.01)

(58) Field of Classification Search
    CPC .......... A61B 2018/00017; A61B 2018/00029; A61B 2018/00041; A61B 2018/00452; A61B 2018/0047; A61B 2018/025; A61B 2018/0256; A61B 2018/0262; A61B 2018/0275; A61B 2018/00458; A61B 2018/00464; A61B 2018/00791; A61B 2017/00747; A61F 7/0085
    USPC ........ 606/20, 22–26; 607/96, 104, 108, 109, 607/111, 114
    See application file for complete search history.

(56) References Cited

U.S. PATENT DOCUMENTS

| | | |
|---|---|---|
| 4,206,609 A | 6/1980 | Durenec |
| 4,946,460 A | 8/1990 | Merry et al. |
| 5,531,742 A | 7/1996 | Barken |
| 5,596,875 A | 1/1997 | Berry et al. |
| 5,759,182 A | 6/1998 | Varney et al. |
| 5,848,981 A | 12/1998 | Herbranson |
| 5,901,707 A | 5/1999 | Goncalves |
| 6,017,337 A | 1/2000 | Pira |
| 6,139,544 A | 10/2000 | Mikus et al. |
| 6,141,985 A * | 11/2000 | Cluzeau ................ A61F 7/0085 606/22 |
| 6,235,018 B1 | 5/2001 | LePivert |
| 6,430,956 B1 | 8/2002 | Haas et al. |
| 6,503,246 B1 | 1/2003 | Har-Shai et al. |
| 6,629,417 B2 | 10/2003 | Haas et al. |
| 6,669,688 B2 | 12/2003 | Svaasand et al. |
| 6,960,202 B2 | 11/2005 | Cluzeau et al. |
| 6,981,970 B2 | 1/2006 | Kami |
| 7,367,341 B2 | 5/2008 | Anderson et al. |
| 7,422,576 B2 | 9/2008 | Boynton et al. |
| 7,630,774 B2 | 12/2009 | Karni et al. |
| 7,751,452 B2 | 7/2010 | Vogler |
| 7,780,656 B2 | 8/2010 | Tankovich |
| 7,850,683 B2 | 12/2010 | Elkins et al. |
| 7,962,192 B2 | 6/2011 | Bodduluri et al. |
| 7,963,959 B2 | 6/2011 | Da Silva et al. |
| 8,150,532 B2 | 4/2012 | Karni et al. |
| 8,435,194 B2 | 5/2013 | Dverin et al. |
| 8,562,597 B2 | 10/2013 | Van Der Heijden et al. |
| 8,579,835 B2 | 11/2013 | Britva et al. |
| 8,764,701 B1 * | 7/2014 | Hicks ................... A61B 18/042 604/23 |
| 8,769,733 B2 | 7/2014 | Galyean et al. |
| 8,950,406 B2 | 2/2015 | Karni et al. |
| 9,050,117 B2 | 6/2015 | Nelson et al. |
| 9,241,753 B2 | 1/2016 | Fourkas et al. |
| 9,522,031 B2 | 12/2016 | Anderson et al. |
| 9,545,284 B2 | 1/2017 | Karni |
| 9,549,773 B2 | 1/2017 | Anderson et al. |
| 9,597,528 B2 | 3/2017 | Schomacker et al. |
| 9,675,419 B2 | 6/2017 | Akeel et al. |
| 9,724,150 B1 | 8/2017 | Bao et al. |
| 9,974,684 B2 | 5/2018 | Anderson et al. |
| 10,118,051 B2 | 11/2018 | Taghizadeh |
| 10,299,871 B2 | 5/2019 | Zingaretti et al. |
| 11,013,547 B2 * | 5/2021 | Rosen .................... A61B 18/02 |
| 2003/0100936 A1 | 5/2003 | Altshuler et al. |
| 2004/0167592 A1 | 8/2004 | Grove et al. |
| 2005/0222565 A1 | 10/2005 | Manstein |
| 2006/0058238 A1 | 3/2006 | Laurent-Applegate et al. |
| 2006/0155267 A1 | 7/2006 | Berzak et al. |
| 2006/0189976 A1 | 8/2006 | Karni et al. |
| 2006/0282067 A1 | 12/2006 | Koop et al. |
| 2007/0088386 A1 | 4/2007 | Babaev |
| 2007/0118098 A1 | 5/2007 | Tankovich |
| 2007/0129714 A1 | 6/2007 | Elkins et al. |
| 2007/0135876 A1 | 6/2007 | Weber |
| 2007/0185527 A1 | 8/2007 | Babaev |
| 2008/0039747 A1 | 2/2008 | Baerwalde et al. |
| 2008/0071332 A1 | 3/2008 | Nelson et al. |
| 2008/0119828 A1 * | 5/2008 | Nelson ................ A61B 18/203 606/9 |
| 2008/0119839 A1 | 5/2008 | Vancelette |
| 2008/0183164 A1 | 7/2008 | Elkins et al. |
| 2008/0183167 A1 | 7/2008 | Britva et al. |
| 2008/0287943 A1 | 11/2008 | Weber et al. |
| 2009/0012585 A1 | 1/2009 | Karni et al. |
| 2009/0171424 A1 | 7/2009 | Britva et al. |
| 2009/0281537 A1 | 11/2009 | Britva et al. |
| 2010/0036295 A1 | 2/2010 | Altshuler et al. |
| 2010/0114007 A1 | 5/2010 | Fischer et al. |
| 2011/0162390 A1 | 7/2011 | Littrup et al. |
| 2011/0313411 A1 | 12/2011 | Anderson et al. |
| 2012/0041525 A1 | 2/2012 | Karni |
| 2012/0071794 A1 | 3/2012 | Karni |
| 2012/0123319 A1 | 5/2012 | Britva et al. |
| 2012/0330194 A1 | 12/2012 | Britva et al. |
| 2014/0007895 A1 | 1/2014 | Britva et al. |
| 2014/0135662 A1 | 5/2014 | Britva et al. |
| 2014/0303696 A1 | 10/2014 | Anderson et al. |
| 2014/0303697 A1 * | 10/2014 | Anderson ............... A61B 18/02 607/104 |
| 2015/0045857 A1 | 2/2015 | Britva et al. |
| 2015/0080991 A1 | 3/2015 | Britva et al. |
| 2015/0216720 A1 | 8/2015 | DeBenedictis et al. |
| 2015/0223975 A1 | 8/2015 | Anderson et al. |
| 2016/0135985 A1 | 5/2016 | Anderson et al. |
| 2016/0157915 A1 | 6/2016 | Anderson et al. |
| 2016/0192961 A1 * | 7/2016 | Ginggen ............. A61B 17/3203 604/173 |
| 2017/0020636 A1 | 1/2017 | Akeel et al. |
| 2017/0065323 A1 | 3/2017 | Rosen et al. |
| 2017/0231721 A1 | 8/2017 | Akeel et al. |
| 2017/0348143 A1 | 12/2017 | Rosen et al. |
| 2018/0028253 A1 | 2/2018 | Anderson et al. |
| 2018/0360520 A1 | 12/2018 | Avalle |
| 2019/0047145 A1 | 2/2019 | Akeel et al. |
| 2019/0239938 A1 | 8/2019 | Kazic et al. |
| 2020/0197104 A1 | 6/2020 | Rosen et al. |

FOREIGN PATENT DOCUMENTS

| | | |
|---|---|---|
| CN | 204814160 U | 12/2015 |
| CN | 106535885 A | 3/2017 |
| DE | 9217897 | 11/1993 |
| EP | 1797847 | 6/2007 |
| EP | 2201917 | 6/2010 |
| EP | 2272455 | 1/2011 |
| GB | 2286660 | 8/1995 |
| JP | 5274026 A | 6/1977 |
| JP | 5416090 A | 2/1979 |
| JP | 04133822 | 5/1992 |
| JP | 10052475 | 2/1998 |
| JP | 2005237908 | 9/2005 |
| JP | 2015504336 A | 2/2015 |
| KR | 200431404 | 11/2006 |
| KR | 100802155 | 2/2008 |
| RU | 2074680 | 3/1997 |
| WO | 2003078596 | 9/2003 |
| WO | 2005096979 | 10/2005 |
| WO | 2006066226 | 6/2006 |
| WO | 2006127467 | 11/2006 |
| WO | 2007064718 | 6/2007 |

(56) References Cited

FOREIGN PATENT DOCUMENTS

| WO | 2008055243 | 5/2008 |
|----|------------|--------|
| WO | 2008083305 | 7/2008 |
| WO | 2008091983 | 7/2008 |
| WO | 2009146053 | 12/2009 |
| WO | 2010017477 | 2/2010 |
| WO | 2013075006 | 5/2013 |
| WO | 2013075016 | 5/2013 |
| WO | 2016022347 A1 | 2/2016 |
| WO | 2017041022 A1 | 3/2017 |
| WO | 2017181156 A1 | 10/2017 |
| WO | 2019089995 A1 | 5/2019 |

OTHER PUBLICATIONS

Gage et al., Critical Temperature for Skin Necrosis in Experimental Cryosurgery, Cryobiology, vol. 19, 1982, pp. 273-282.
Gage et al., Sensitivity of Pigmented Mucosa and Skin to Freezing Injury, Cryobilogy, vol. 16, 1979, pp. 348-361.
Har-Shai et al., Effect of Skin Surface Temperature on Skin Pigmentation During Contact and Intralesional Cryosurgery of Hypertrophic Scars and Kleoids, Journal of the European Academy of Dermatology and Venereology, vol. 21, No. 2, Feb. 2007, pp. 191-198.
Thai et al., Cryosurgery of Benign Skin Lesions, Australasian Journal of Dermatology, vol. 40, 1999, pp. 175-186.
Yeh, Cryosurgical Treatment of Melanin-Pigmented Gingiva, Oral Surgery, Oral Medicine, Oral Pathology, Oral Radiology, and Endodontology, vol. 86, Issue 6, Jun. 1998, pp. 660-663.
Zachariassen et al., Ice Nucleation and Antinucleation in Nature, Cryobiology, vol. 41, Issue 4, Dec. 2000, pp. 257-279.

\* cited by examiner

DERMATOLOGICAL CRYOSPRAY DEVICES HAVING LINEAR ARRAY OF NOZZLES AND METHODS OF USE

CROSS-REFERENCE TO RELATED APPLICATIONS

The present application is a continuation of U.S. patent application Ser. No. 16/020,852, filed Jun. 27, 2018, issued as U.S. Pat. No. 11,013,547 on May 25, 2021, and titled "DERMATOLOGICAL CRYOSPRAY DEVICES HAVING LINEAR ARRAY OF NOZZLES AND METHODS OF USE," which claims priority from U.S. Patent Application No. 62/527,652, filed Jun. 30, 2017, and titled, "DERMATOLOGICAL CRYOSPRAY DEVICES HAVING LINEAR ARRAY OF NOZZLES AND METHODS OF USE," the entirety of each of which are hereby incorporated by reference herein.

BACKGROUND

Cryotherapy is the local or general use of cold in medical therapy. Cryotherapy can include the controlled freezing of biological tissue, which controlled freezing of biological tissue, such as skin tissue, can produce various effects. Certain tissue freezing procedures and devices, such as conventional cryoprobes, can cause severe freezing of tissue and generate cellular and visible skin damage.

There is a demand for dermatologic products that can lighten the appearance of skin or otherwise controllably affect skin pigmentation. For example, it may be desirable to lighten the overall complexion or color of a region of skin to alter the general appearance for cosmetic reasons. Also, lightening of particular hyperpigmented regions of skin, such as freckles, 'café au lait' spots, melasma, or dark circles under the eyes that may result from excessive local amounts of pigment in the skin, may also be desirable for cosmetic reasons. Hyperpigmentation can result from a variety of factors such as UV exposure, aging, stress, trauma, inflammation, etc. Such factors can lead to an excess production of melanin, or melanogenesis, in the skin by melanocytes, which can lead to formation of hyperpigmented areas. Such hyperpigmented areas may be associated with excess melanin within the epidermis and/or dermal-epidermis junction. However, hyperpigmentation can also result from excess melanin deposited within the dermis.

Hypopigmentation of skin tissue has been observed as a side effect in response to temporary cooling or freezing of the tissue, such as may occur during conventional cryosurgery procedures. Loss of pigmentation following skin cooling or freezing may result from decreased melanin production, decreased melanosome production, destruction of melanocytes, or inhibited transfer or regulation of melanosome into the keratinocytes in the lower region of the epidermal layer. The resultant hypopigmentation may be long-lasting or permanent. However, it has also been observed that some of these freezing procedures can generate regions of hyperpigmentation (or skin darkening) of skin tissue. The level of increase or decrease in pigmentation may be dependent upon certain aspects of the cooling or freezing conditions, including the temperature of the cooling treatment, and the length of time the tissue is maintained in a frozen state.

Improved hypopigmentation treatments, devices, and systems have been developed to improve the consistency of skin freezing and the overall hypopigmentation consistency. For example, it has been observed that moderate degrees of freezing (e.g., −4 to −30 degrees Celsius) at shorter time frames (e.g., 30 to 60 seconds) can produce particular dermatological effects, such as affecting the expression of skin pigmentation (e.g., hypopigmentation). Cryotherapy can be provided using a variety of techniques including the direct application of a cryogen spray to the skin of the patient or the application of a cooled probe or plate to the skin of the patient. Exemplary methods and devices are described in: U.S. Patent Publication No. 2011/0313411, filed on Aug. 7, 2009, and entitled "METHOD AND APPARATUS FOR DERMATOLOGICAL HYPOPIGMENTATION"; U.S. Patent Publication No. 2014/0303696, filed on Nov. 16, 2012, and entitled "METHOD AND APPARATUS FOR CRYOGENIC TREATMENT OF SKIN TISSUE"; U.S. Patent Publication No. 2014/0303697, filed on Nov. 16, 2012, and entitled "METHOD AND APPARATUS FOR CRYOGENIC TREATMENT OF SKIN TISSUE"; U.S. Patent Publication No. 2015/0223975, filed on Feb. 12, 2015, and entitled "METHOD AND APPARATUS FOR AFFECTING PIGMENTATION OF TISSUE"; U.S. Patent Publication No. 2017/0065323, filed on Sep. 6, 2016, and entitled "MEDICAL SYSTEMS, METHODS, AND DEVICES FOR HYPOPIGMENTATION COOLING TREATMENTS", the entirety of each of which is hereby incorporated by reference herein.

While the treatment of skin or a localized lesion to affect pigmentation can be accomplished with cryotherapy, it may be desirable to provide improved methods, systems, and devices for cryotherapy. In particular, improved designs, controls and parameters associated with cryogen delivery to achieve consistent and reliable skin freezing and desired skin treatment effect may be of benefit. Accordingly, improved dermatological cryospray methods, systems, and devices are desirable.

BRIEF SUMMARY

The present invention relates to improved systems, devices, and methods of delivery of a cryogen to the skin of a patient for skin treatment. More specifically, the present invention relates to improved dermatological cryospray methods, devices, and systems that provide consistency of skin treatment by reliably freezing the skin during treatment while limiting adverse side effects from the skin freezing. Exemplary embodiments include a nozzle design comprising a linear array of orifices. This linear array of orifices can deliver a linear spray of cryogen or cold gas to the skin surface when cryogen or cold gas is dispensed through those orifices. Advantageously, this linear spray application provides a line of cooling treatment that facilitates uniform and even treatment of large areas of skin. The linear cooling treatment facilitates a sweeping delivery of cryogen or cold gas to a patient's skin by uniformly delivering cryogen or cold gas through the linear array of orifices. Uniformly and consistently treating large areas of skin may be of particular benefit for a variety of skin indications, such as pigmentation or coloration related indications including hypopigmentation or hyperpigmentation; acne; rosacea; psoriasis melasma; lentigines; freckle; birthmark, liver spot, age spot, or café au lait macule.

One aspect of the present disclosure relates to a method of cooling an area of skin of a patient. This method includes: positioning a cryospray applicator to a position proximate to the area of the skin tissue of the patient to be treated; and directing a planar spray of cyrogen through a linear array of orifices of the cryospray applicator to cool the area of the skin tissue of the patient in a line of cooling treatment to effect a treatment of the skin.

In some embodiments, this method includes heating a tank containing liquid and gaseous cryogen with a tank heater such that the tank maintains a desired pressure. In some embodiments, the cryogen can include: a liquid cryogen; a gaseous cryogen; a two-phase fluid; cooled air; and/or carbon dioxide. In some embodiments, directing the planar spray of cryogen or cold gas through the linear array of orifices includes transporting cryogen such as liquid cryogen from the tank to an applicator via a supply tube. In some embodiments, a pressure of the liquid cryogen in the supply tube is substantially equal to the desired pressure in the tank. In some embodiments, the method includes moving the cryospray applicator so as to provide a linear curtain of cooling treatment to the area of the skin tissue of the patient. In some embodiments, directing the planar spray of liquid cryogen or cold gas through the linear array of orifices includes locally freezing an epidermis to alter a pigmentation of the area of the skin tissue of the patient.

In some embodiments, directing the planar spray of cryogen, which can include liquid cryogen, cold gas, or two-phase fluid including liquid cryogen and gas, through the linear array of orifices includes locally disrupting an epidermis to produce gradual skin lightening in the area of the skin tissue of the patient. In some embodiments, the planar spray of cryogen can comprise one or several liquid cryogen droplets, and in some embodiments, the liquid cryogen can be liquid carbon dioxide. In some embodiments, the planar spray of liquid cryogen has a temperature at the skin surface of between −4 C to −80 C.

In some embodiments, each orifice can be and/or include a cylindrical opening. In some embodiments, the linear array of orifices can be a single row of orifices or a plurality of rows of orifices. In some embodiments, the method includes delivering a gas to form a protective curtain through which the liquid cryogen or cold gas moves downstream of the orifices. In some embodiments, the protective curtain prevents water entrainment or ambient air entrainment as the liquid cryogen or cold gas moves downstream of the orifices. In some embodiments, the gas is expelled from the orifices before or during the directing the planar spray of liquid cryogen or cold gas from the orifices. In some embodiments, the gas includes at least one of: a dry gas; or an inert gas.

In some embodiments, positioning the cryospray applicator to the position proximate to the area of the skin tissue of the patient includes contacting the area of skin tissue of the patient with a mechanical spacer to maintain a predetermined distance between the cryospray applicator and the skin tissue. In some embodiments, the predetermined distance includes a range from 0.125 inches to 3 inches. In some embodiments, the mechanical spacer includes at least one of: a wheeled spacer; and a sliding spacer. In some embodiments, positioning the cryospray applicator to the position proximate to the area of the skin tissue of the patient to be treated includes positioning a non-contact cryospray applicator proximate to the area of the skin tissue of the patient.

In some embodiments, the method includes applying a mask to the area of the skin tissue of the patient prior to directing the planar spray of liquid cryogen or cold gas from the linear array of orifices. In some embodiments, the mask can be a perforated film. In some embodiments, the method includes warming the area of skin tissue of the patient after the cooling treatment. In some embodiments, the area of skin tissue of the patient is warmed by delivery of warm gas or liquid from the same or different orifices for convective warming.

One aspect of the present disclosure relates to a skin cooling treatment system. The system includes: a cryogen source; a non-contact cryospray applicator fluidly coupled to the cryogen source, which cryospray applicator can direct a planar spray of liquid cryogen to an area of skin tissue of a patient to be treated, which non-contact cryospray applicator includes a linear array of orifices that can spray the liquid cryogen or cold gas to cool the area of the skin tissue of the patient in a line of cooling treatment.

In some embodiments, the treatment system includes a supply tube fluidly coupling to a bottom portion of the cryogen source. In some embodiments, the cryogen source further includes a heater to maintain the cryogen source at a desired pressure or temperature range. In some embodiments, the desired temperature range can include a temperature above an ambient temperature. In some embodiments, the cryogen source includes a liquid and gaseous cryogen. In some embodiments, the linear array of orifices includes a single row of orifices or a plurality of rows of orifices. In some embodiments, the orifices in the linear array of orifices have the same dimensions, or have different dimensions. In some embodiments, the orifices are uniformly spaced or at least some of the orifices are staggered. In some embodiments, each orifice includes a cylindrical opening.

In some embodiments, the non-contact cryospray applicator further includes a nozzle tube and a shroud extending at least partially around the linear array of orifices of the nozzle tube. In some embodiments, the shroud creates a stagnation zone at distal openings of the orifices. In some embodiments, the nozzle tube can be made from a first material and the shroud can be made from a second material. In some embodiments, the second material of the shroud has a lower thermal conductivity than the first material of the nozzle tube. In some embodiments, the shroud has a depth equal to at least two times a diameter of one of the orifices of the linear array of orifices. In some embodiments, the treatment system includes a temperature control mask or a perforated film. The temperature control mask or perforated skin can contact the area of the skin tissue of the patient.

One aspect of the present disclosure relates to a cryospray device for delivering a cryogen to a patient's skin for altering a pigmentation appearance. The cryo—spray device includes: an applicator including a head portion; a supply channel extending at least partially through the head portion; and a nozzle assembly coupled to the head portion and fluidly coupled to the supply channel, the nozzle assembly including a linear array of orifices that can spray the cryogen to cool an area of a skin tissue of the patient in a linear cooling treatment to alter a pigmentation appearance thereof.

In some embodiments, the linear array of orifices includes a single row of orifices or a plurality of rows of orifices. In some embodiments, each orifice includes a cylindrical opening. In some embodiments, the nozzle assembly includes a nozzle tube and a shroud extending at least partially around the linear array of orifices. In some embodiments, the shroud creates a stagnation zone at distal openings of the orifices. In some embodiments, the nozzle tube can be made from a first material and the shroud can be made from a second material. In some embodiments, the second material of the shroud has a lower thermal conductivity than the first material of the nozzle tube. In some embodiments, the shroud has a depth equal to at least two times a diameter of one of the orifices of the linear array of orifices.

In some embodiments, the cryospray device includes a filter located within the head portion and upstream of the linear array of orifices. In some embodiments, the filter includes a sintered metal filter. In some embodiments, the cryospray device includes an array of curtain apertures in the nozzle assembly. In some embodiments, the array of curtain apertures can be configured to deliver a protective gas to prevent water entrainment or ambient air entrainment as the liquid cryogen or cold gas moves downstream of the orifices.

In some embodiments, the cryospray device includes a mechanical spacer coupled to the head portion. In some embodiments, the mechanical spacer can maintain at least a minimum or constant distance between the linear array of orifices and a surface of the patient's skin. In some embodiments, the mechanical spacer is adjustable to change the minimum distance. In some embodiments, the mechanical spacer includes a wheeled spacer. In some embodiments, the wheeled spacer includes a first wheel located proximate to a first end of the linear array of orifices and a second wheel located proximate to a second end of the linear array of orifices. In some embodiments, the mechanical spacer includes a slider spacer, and in some embodiments, the slider spacer includes a plurality of adjustable legs or prongs. In some embodiments, the applicator further includes a handle portion sized and shaped to be held by an operator of the cryospray device.

Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The invention will be better understood upon reading the following description and examining the figures which accompany it. These figures are provided by way of illustration only and are in no way limiting on the invention.

DETAILED DESCRIPTION

Figure 1:
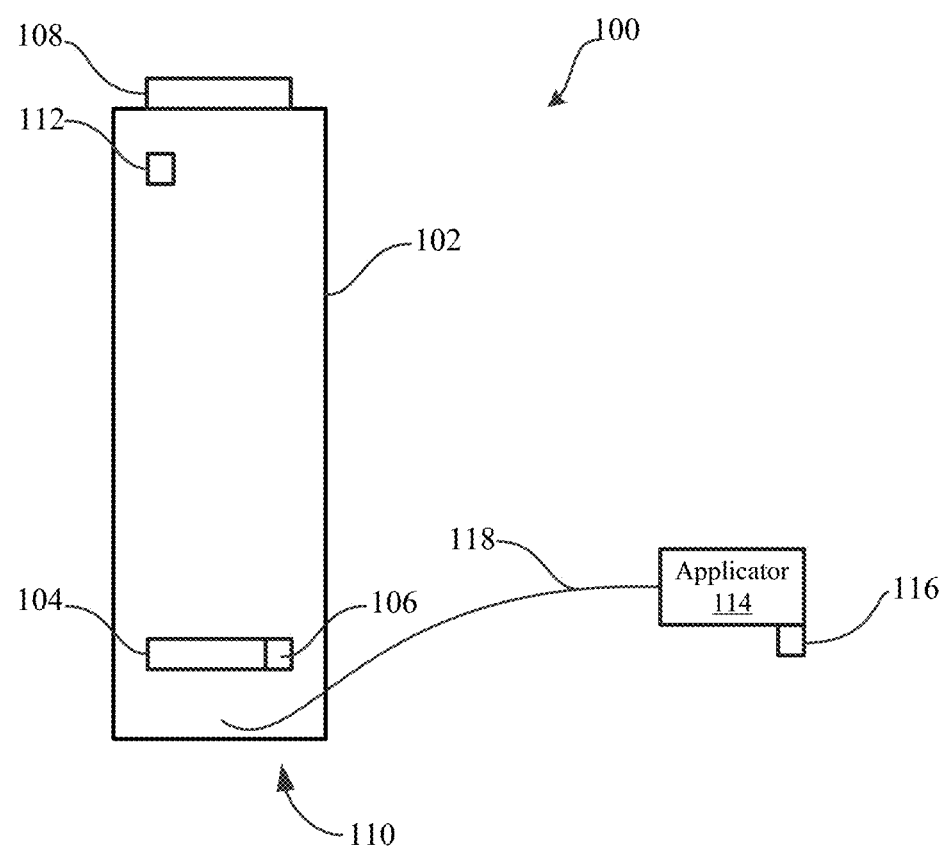
FIG. 1 is a schematic illustration of one embodiment of a cryogenic treatment system.

Embodiments of the present disclosure relate to systems, methods, and devices for providing cryotherapy skin treatments. In some embodiments, these can include a cryospray applicator utilizing a nozzle comprising a linear array of orifices to direct cryogen or cold gas toward the skin in a planar manner that produces a line of frozen tissue to effect the desired skin treatment, such as skin lightening or hypopigmentation. The linear array of orifices can be arranged in a single row of orifices or in a plurality of rows of orifices. This linear array nozzle design can direct a curtain application of cryogen or cold gas such that it impinges on the skin surface, which can facilitate uniform and controlled application of cooling treatment to large treatment areas of the skin of a patient without undesirable side effects.

The fine-tuned linear array nozzle design of the present invention provides advantages over conventional spray nozzle designs, which frequently include a single opening or a cluster of openings. For example, a single opening has limited treatment area and is difficult to provide uniform cooling treatment when sprayed over an area. A cluster of openings may provide a larger treatment area, but the cluster of openings may undesirably increase an intensity of the cryogen or cold gas spray against the patient's skin resulting in undesirable blasting on the skin and lack of control. Conventional nozzle designs may also increase the difficulty of providing reliable and consistent cryospray dosing over large areas of skin tissue. In contrast, nozzles of the present disclosure comprise a linear array of orifices to facilitate uniform and even delivery of cryogen or cold gas toward large areas of the skin in a planar manner that produces a line of skin treatment. This linear coverage facilitates sweeping of the nozzle over the skin, while delivering controlled and consistent dosing of cryogen to the skin.

The nozzle can include features and/or be controlled to prevent obstruction of some or all of the orifices in the linear array of orifices and/or to prevent the entrainment of undesired amounts of moisture in dispensed cryogen. These features can include a shroud that can be part of the nozzle. The shroud can extend wholly or partially around the linear array of orifices. The shroud can, in some embodiments, decrease the likelihood of ice crystals forming at the orifices and thereby block flow of cryogen through the orifices.

The nozzle can further include one or several orifices from which a protective gas can be dispensed. In some embodiments, this protective gas can form a protective curtain through or inside of which the cryogen can be dispensed to prevent the entrainment of ambient moisture in the cryogen and to prevent icing of the nozzle surface during or following the spray or cryogen. The protective gas can be dispensed from the same orifices or applicator from which the cryogen is dispensed by delivering the protective gas before or after the delivery of the cryogen, or the protective gas can be delivered from separate orifices than those from which the cryogen is dispensed. The protective gas can be, in some embodiments, nitrogen, carbon dioxide, helium, hydrogen, neon, oxygen, fluorine, argon, methane, a refrigerant, and/or air. In some embodiments, the protective gas can be an inert gas.

With reference now to FIG. 1, one embodiment of a cryogenic treatment system 100 is shown. The cryogenic treatment system 100 can contain and/or deliver a cryogen. This cryogen can include, in some embodiments, a liquefied gas such as liquid helium, liquid hydrogen, liquid neon, liquid oxygen, liquefied fluorine, liquefied argon, liquefied methane, liquefied air, or the like. In some embodiments, the cryogen can include a cooled or cold gas such as, for example cooled or cold air. In some embodiments, the cryogen in the tank can be a mixture of liquid and gas such as a liquid and gaseous cryogen, or in other words, can be partially liquid. The cryogenic treatment system 100 can include a tank 102, also referred to herein as a container 102, a cryogen source 102, or a canister 102. The tank 102 can comprise a variety of shapes and sizes and can be made from a variety of materials. In some embodiments, the tank 102 can comprise a metal cylinder defining an internal volume that can contain the cryogen and/or they can contain pressurized cryogen. In some embodiments, the metal cylinder can be made of aluminum or steel.

The tank 102 can, in some embodiments, include a heater 104, a thermostat 106, and/or controller 108. The heater 104 can comprise any desired heater capable of heating the tank 102 and/or the cryogen contained in the tank 102 to a desired temperature and/or until the cryogen contained in the tank 102 attains a desired pressure. The desired pressure can be, in some embodiments, less than 100 psi, less than 500 psi, less than 1,000 psi, less than 2,000 psi, less than 5,000 psi, between 0 and 2,000 psi, between 500 and 1,500 psi, approximately 1,000 psi, or any other or intermediate pressure. In some embodiments, the heater 104 can be located at or on a bottom 110 of the tank 102 and/or proximate to the bottom 110 of the tank 102. In some embodiments, this location of the heater 104 on and/or in the tank 102 can facilitate heating of the cryogen contained within the tank 102 and specifically the heating of a liquid portion of the cryogen contained within the tank.

The thermostat 106 can comprise one or several features configured to measure the temperature within the tank 102. These can include, for example, one or several thermocouples, thermistors, thermometers, or the like. The thermostat 106 can be positioned at any desired location on the tank 102 and can, in some embodiments, be positioned proximate to the heater 104.

The controller 108 can be communicatively coupled with the heater 104 and/or with the thermostat 106. In some embodiments, the controller 108 can include one or several features that display one or several attributes of the tank 102 and/or the cryogen such as, for example, the pressure in the tank 102, the amount of cryogen in the tank 102, the temperature of the cryogen or the tank 102, or the like. The controller 108 can further include one or several features whereby set point information can be provided by the user to the controller and/or whereby set points can be changed.

The controller 108 can, via the communicative coupling with the heater 104 and/or with the thermostat 106 control the temperature of the cryogen and/or of the tank 102. In some embodiments, for example, the controller can receive one or several signals indicative of a temperature of the cryogen and/or of the tank 102 from the thermostat 106. The controller can compare the signals to set point information and can determine whether to increase or decrease the temperature of the cryogen and/or of the tank 102. Control the temperature of the cryogen and/or of the tank by, for example, controlling the powering of the heater 104 such as by, for example, controlling the amount of current going to the heater 104. In some embodiments, the controller 108, the heater 104, and the thermostat 106 can sufficiently heat the tank 102 to maintain a constant pressure and/or temperature during dispensing of the cryogen.

The tank 102 can include a switch 112 such as a safety switch. In some embodiments, the safety switch can be communicatively coupled with the controller 108 and/or the heater 104. In some embodiments, manipulation of the switch 112 can cut power to the heater 104 to prevent any further heating of the tank 102 and/or of the cryogen in the tank 102. In some embodiments, the switch 112 can be separate from the controller 108, and in some embodiments, the switch 112 can be integrated in the controller 108.

The cryogenic treatment system 100 can include an applicator 114, also referred to herein as a cryospray applicator 114, which applicator 114 can include a nozzle 116, also referred to herein as a nozzle assembly 116, that can include a linear array of orifices. In some embodiments, the cryospray applicator 114 can be a non-contact cryospray applicator in that the nozzle 116 or other portion of the applicator 114 does not contact the skin of the patient to cool the skin of the patient, but rather the cryogen is dispensed by the nozzle 116 to the skin of the patient to cool the skin of the patient.

The applicator 114, and specifically the nozzle 116 can dispense cryogen from the tank 102 to the skin of the patient. In some embodiments, the applicator 114 can be fluidly connected with the tank 102 via a tube 118, also referred to herein as the hose 118, the supply tube 118, or connecting tube 118. In some embodiments, the tube 118 can be fluidly connected with the internal volume of the tank via a port or aperture extending through the tank. In some embodiments, the tube 118 can connect to the tank 102 at or proximate to the bottom 110 of the tank 102. The connection of the tube 118 at or proximate to the bottom 110 of the tank 102 can facilitate the drawing of cryogen, and specifically the drawing of liquid cryogen into the tube 118 and the delivering of cryogen, and specifically the delivering of liquid cryogen to the applicator 114 and the nozzle 116.

The tube 118 can comprise a variety of shapes and sizes and can be made from a variety of materials. In some embodiments, the tube can be made from a material that is able to withstand the temperature and/or pressure of the cryogen and/or to withstand the cryogen. In some embodiments, the tube 118 can have a diameter, a shape, and/or a link such that the pressure of the cryogen at the nozzle 116 and/or at the applicator 114 is the same or substantially the same as at the tank 102. As used herein, substantially or approximately referred to a value deviating by less than 10%, 5%, 2%, or 1% from the value or values with which they are associated. Thus, the pressure of the cryogen at the nozzle 116 and/or at the applicator 114 is the same or substantially the same as in the tank when the pressure of the cryogen at the nozzle 116 and/or at the applicator 114 deviates by less than 10%, 5%, 2%, or 1% from the pressure of the cryogen in the tank 102.

Figure 2:
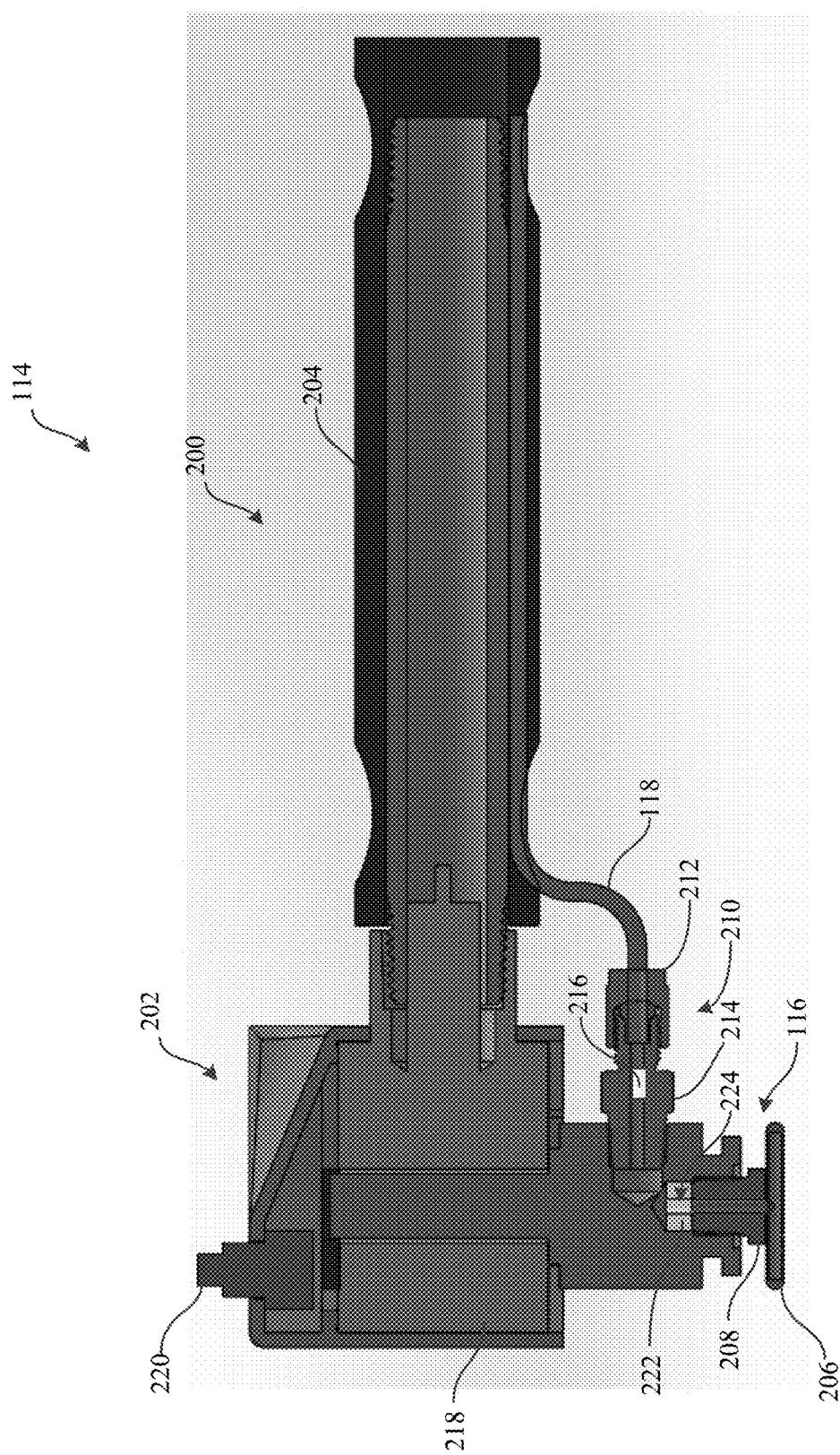
FIG. 2 is a side-section view of one embodiment of an applicator of a cryogenic treatment system.

FIG. 2 is a side-section view of one embodiment of the applicator 114 including the nozzle 116. The applicator 114 can comprise a variety of shapes and sizes and can be made from a variety of materials. In some embodiments, the applicator 114 can be a hand-held applicator 114, and in other embodiments, the applicator 114 can be part of an automated system or device such as a robotic system or device, a teleoperated system or device, or the like.

The applicator 114 can include a handle portion 200 and a head portion 202. The handle portion 200 can include a grip 204 connected to the head portion 202. The grip 204 can be sized and shaped to be held in the hand of an operator of the applicator 114. The head portion 202 can connect to the nozzle 116 and can specifically be coupled to an elongate member 206, also referred to herein as a nozzle tube 206, of the nozzle 116 via a nozzle base 208. In some embodiments, the nozzle base 208 can comprise a threaded plug such as, for example, a NPT threaded plug. The nozzle base 208 can be made from a variety of materials including, for example, brass, steel, stainless steel, nickel, a nickel alloy, or the like.

As seen in FIG. 2, the tube 118 can extend along the grip 204 and can couple to the head portion 202 at coupling 210. The coupling 210 can include, for example, a hose coupler 212 that can include, for example, a female hose coupling. The hose coupler 212 can threadingly engage with a head coupler 214, which head coupler 214 can be, for example, a threaded coupling. In some embodiments, and as depicted in FIG. 2, the head coupler 214 threadingly engages features of the head portion 202 of the applicator 114 to couple the head coupler 214 to the head portion 202.

The applicator 114 can include a filter 216. The filter 216 can comprise a variety of shapes and sizes and can be made from a variety of materials. The filter 216 can be located in numerous positions throughout the applicator 114 and/or the tube 118. In some embodiments, the filter 216 can be located between the tube 118 and the nozzle 116, in the nozzle 116 such as in, for example, the nozzle base 208, in the coupling 210 such as, for example, in the head coupler 214, or the like.

The filter 216 can be sized to eliminate and/or minimize clogs at the nozzle 116. In some embodiments, the filter 216 can be a 1μ filter, a 10μ filter, a 25μ filter, a 50μ filter, 100μ filter, a between 10μ and 100μ filter, a between 40μ and 50μ filter, an approximately 50μ filter, or any other desired filter. In some embodiments, the filter 216 can comprise a ceramic filter, a polymer filter, a sintered metal filter, or any other desired filter type. In some embodiments, the filter 216 can comprise a sintered stainless steel filter or mesh screen.

The head portion 202 of the applicator 114 can include a valve 218 that can control the flow of cryogen to the nozzle 116 and/or the dispensing of cryogen from the nozzle 116. The valve 218 can, in some embodiments, be controlled by a control feature 220 that can be, for example, a button. In some embodiments, for example, manipulation of the control feature 220 can result in the opening or closing of the valve 218 and can thus result in the initiation or the termination of dispensing of cryogen. The head portion 202 of the applicator 114 can, in some embodiments, include a filler plug 222. In some embodiments, the filler plug 222 can comprise a dead volume filler plug and can be located in a supply channel 224 of the head portion 202 proximate to the nozzle 116 and specifically proximate to the nozzle base 208. In some embodiments, the supply channel 224 can extend through at least a portion of the head portion 202 of the applicator. In some embodiments, the valve 218 interacts with the filler plug 222 to provide cryogen to the nozzle 116 and/or to dispense cryogen from the nozzle 116.

Figure 3:
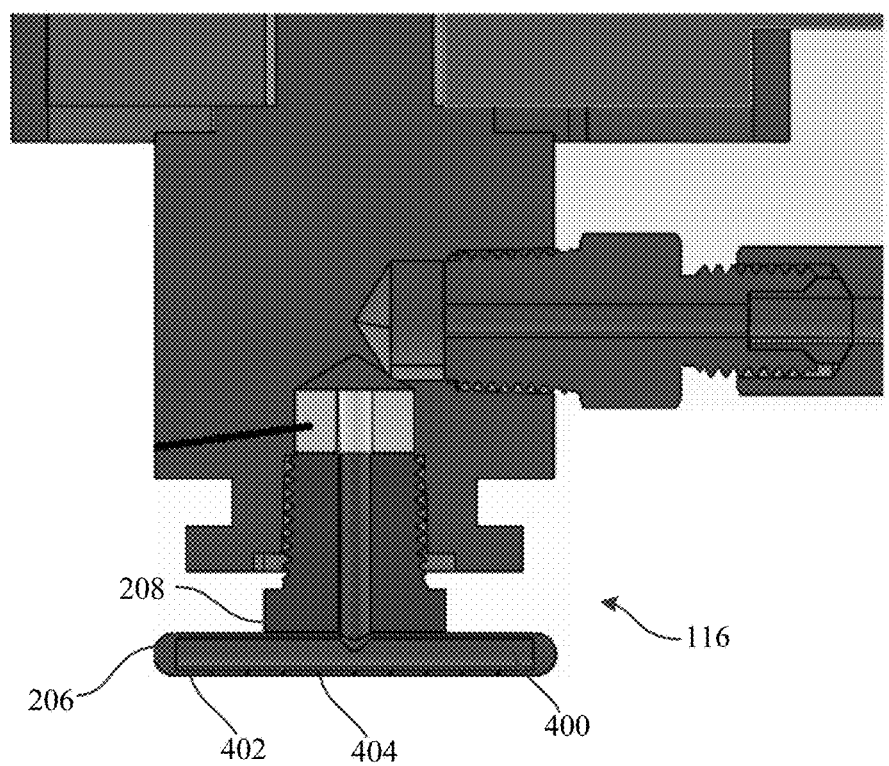
FIG. 3 is a side-section, close-up view of aspects of a head portion of an applicator.
Figure 4:
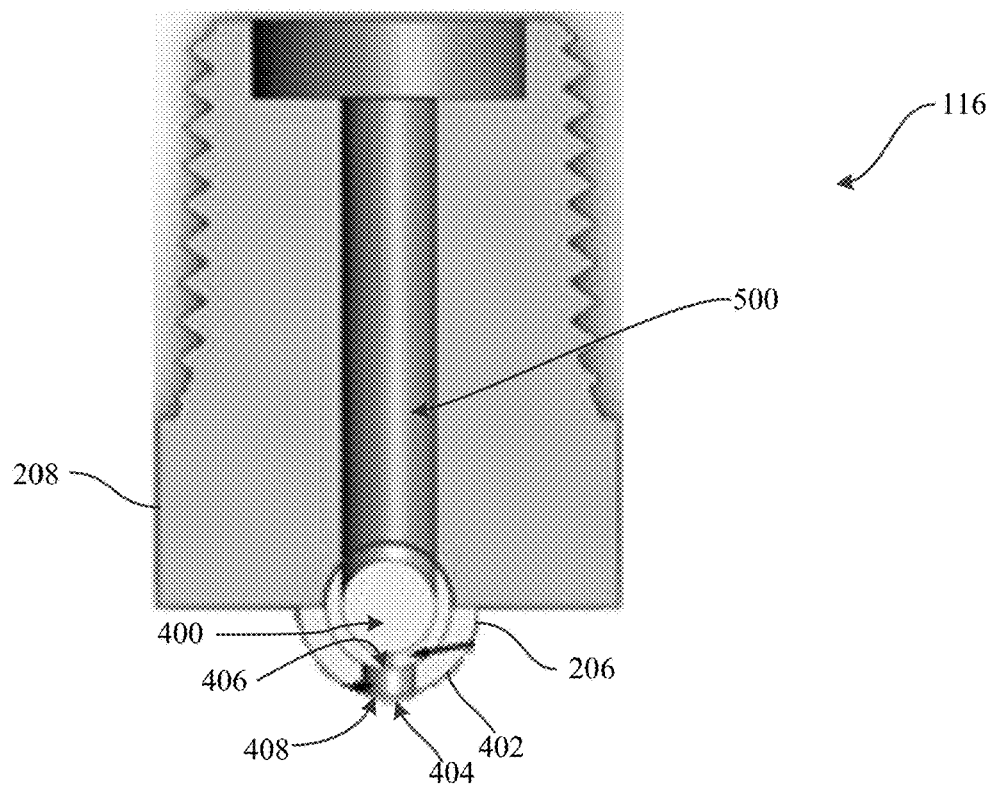
FIG. 4 is a front-section, close-up view of a nozzle including an elongate member.

As seen in the side-section, close-up view of FIG. 3 and in the front-section, close-up view of FIG. 4, the elongate member 206 of the nozzle includes an internal volume 400 defined by walls 402 of the elongate member 206. A plurality of orifices 404, some or all of which can comprise a cylindrical aperture or cylindrical opening and thus can be cylindrical orifices 404, extend through the walls 402 of the elongate member 206 to fluidly couple the internal volume 400 of the elongate member 206 to outside of the elongate member 206. Specifically, the orifices 404 extend from a proximal opening 406 contacting the internal volume 400 of the elongate member 206 to distal openings 408. As seen FIG. 4, a channel 500 extending through the nozzle base 208 fluidly connects with the internal volume 400 of the elongate member 206. The channel 500 can further fluidly connect with the tube 118 and/or with the valve 218 or the fill plug 222.

In some embodiments, the orifices 404 can each have the same, or approximately the same diameter and/or depth, and in some embodiments, some or all of the orifices 404 can have different diameters and/or depths. In some embodiments, the orifices 404 can be sized and shaped so that the expansion of cryogen passing through the orifices 404 is a nearly adiabatic expansion. In some embodiments, for example, each orifice 404 can have a diameter of: approximately 0.001 inches, approximately 0.005 inches, approximately 0.007 inches, approximately 0.008 inches, approximately 0.01 inches, approximately 0.02 inches, approximately 0.05 inches, approximately 0.08 inches, approximately 0.1 inches, between approximately 0.001 and 0.01 inches, between approximately 0.005 and 0.008 inches, or any other or intermediate diameter. In some embodiments, the orifices can have a depth of approximately 0.001 inches, approximately 0.005 inches, approximately 0.008 inches, approximately 0.01 inches, approximately 0.02 inches, approximately 0.05 inches, approximately 0.08 inches, approximately 0.1 inches, approximately 0.5 inches, between approximately 0.001 and 0.05 inches, between approximately 0.005 and 0.02 inches, and/or any other or intermediate depth.

Figure 5:
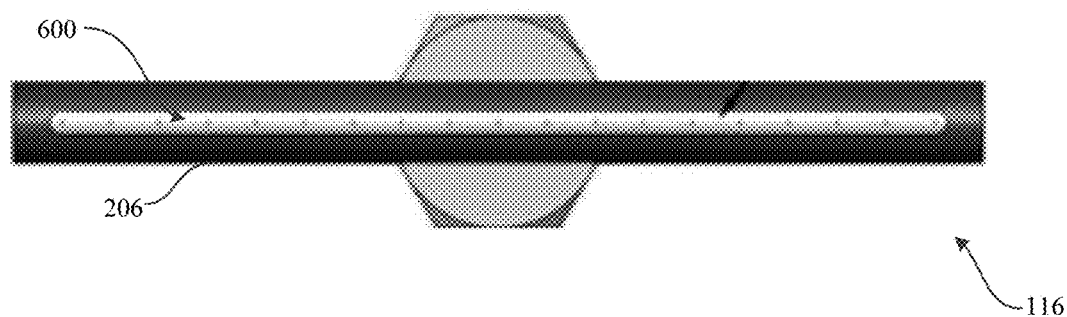
FIG. 5 is a bottom view of one embodiment of a nozzle and an elongate member including a linear array of orifices.
Figure 6:
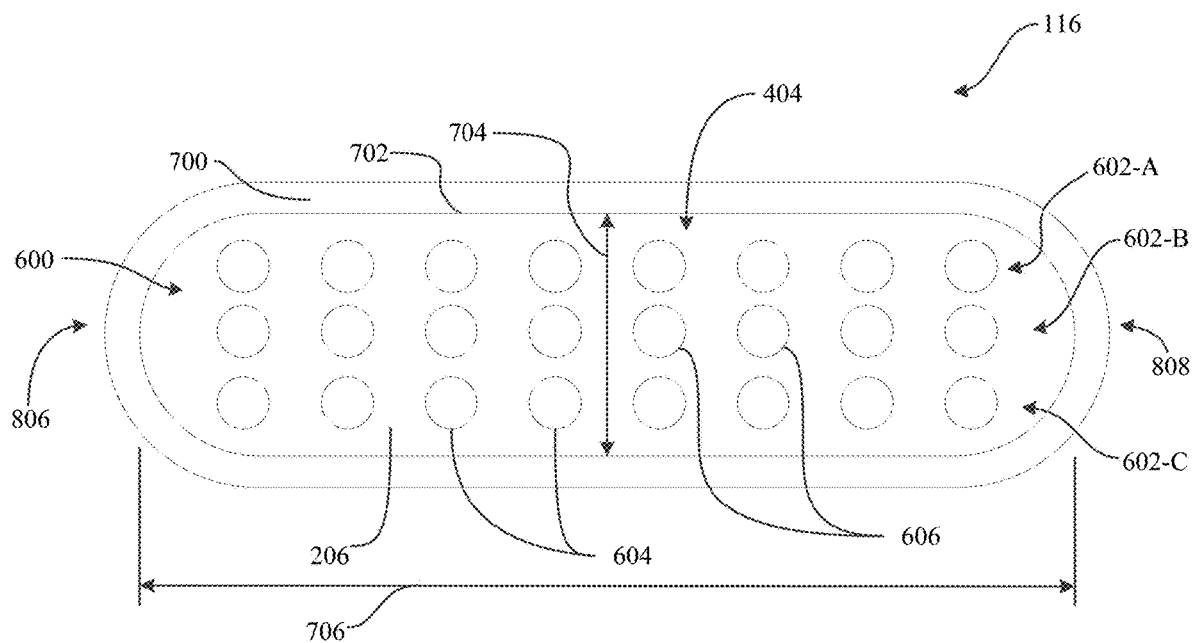
FIG. 6 is a schematic illustration of one embodiment of a linear array of uniformly spaced orifices located on an elongate member of a nozzle.
Figure 7:
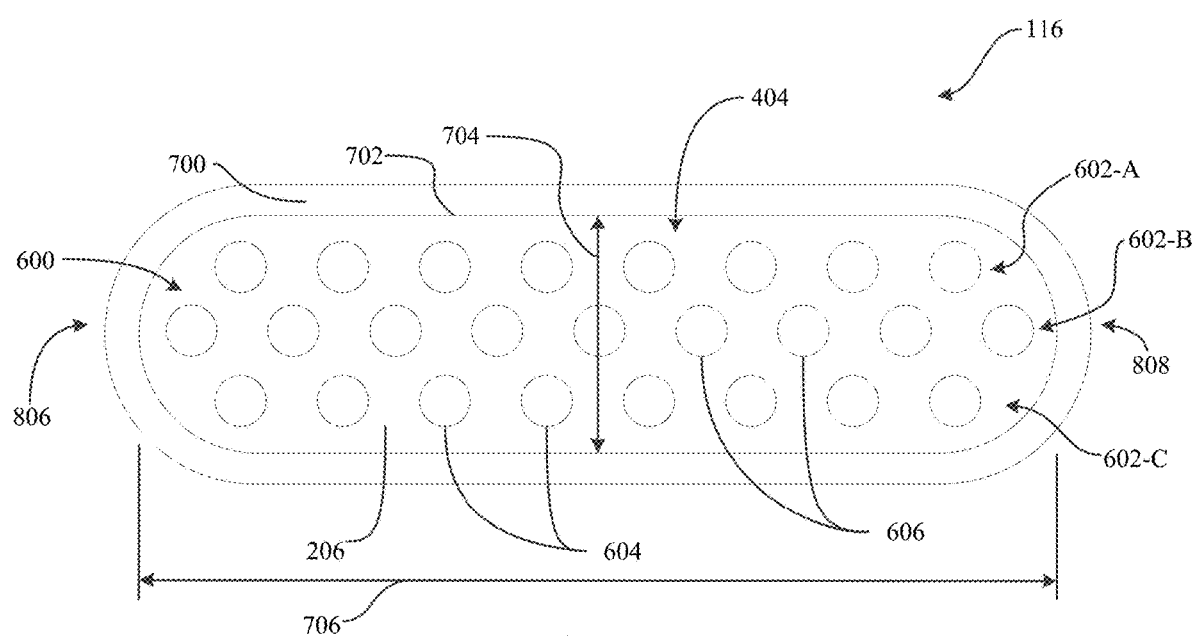
FIG. 7 is a schematic illustration of one embodiment of a linear array of staggered orifices located on an elongate member of a nozzle.

In some embodiments, and as seen in FIGS. 5 through 7, the plurality of orifices 404 can be arranged in a linear array 600 of orifices 404. This array 600 of orifices 404 can include, for example, 3 orifices, 5 orifices, 8 orifices, 10 orifices, 11 orifices, 15 orifices, 20 orifices, 30 orifices, 50 orifices, 100 orifices, between 0 and 100 orifices, between 0 and 50 orifices, between 0 and 25 orifices, between 0 and 11 orifices, or any other or intermediate number of orifices. In some embodiments, the linear array 600 can have a length of approximately 10 inches, approximately 5 inches, approximately 2 inches, approximately 1 inch, approximately 0.5 inches, between 0 and 10 inches, between 0 and 5 inches, between 0 and 2 inches, or any other or intermediate length. In some embodiments, each of the nozzles can be separated by a distance of: approximately 1 inch, approximately 0.5 inches, approximately 0.1 inches, approximately 0.05 inches, approximately 0.01 inches, between 0 and 1 inches, between 0 and 0.5 inches, between 0 and 0.2 inches, or any other or intermediate distance.

In some embodiments, the plurality of orifices 404 forming the linear array of orifices can be arranged in a single row of orifices as shown in FIG. 5, or in a plurality of rows 602-A, 602-B, 602-C of orifices 404. In some embodiments, the linear array 600 can comprise one row of orifices, two rows of orifices, three rows of orifices, 5 rows of orifices, 7 rows of orifices, 10 rows of orifices, 20 rows of orifices, between 1 and 10 rows of orifices, or any other or intermediate number of rows of orifices. In some embodiments, each of the rows 602-A, 602-B, 602-C of orifices 404 can have the same number of orifices 404, and in some embodiments, some or all of the rows 602-A, 602-B, 602-C of orifices 404 can have a different number of orifices. In embodiments in which the linear array 600 comprises multiple rows of orifices 404, the orifices 404 in the different rows can be aligned as shown in FIG. 6, or the orifices can be staggered as shown in FIG. 7. In some embodiments, the orifices 404 in the different rows of orifices 404 can have the same size or dimensions, and in some embodiments, the orifices can have different sizes or dimensions. In some embodiments, some or all of the orifices 404 in the linear array 600 can be equally and/or uniformly spaced, and in some embodiments, some or all of the orifices 404 in the linear array 600 can be unequally spaced and/or staggered.

In some embodiments, some or all of the plurality of orifices 404 can dispense the cryogen, and in some embodiments, some or all of the plurality of orifices 404 can dispense a protective gas such as an inert gas. In some embodiments, this inert gas can have a desired water content such as, for example, less than 10% water by weight, less than 5% water by weight, less than 1% water by weight, less than 0.1% water by weight, less than 0.05% water by weight, less than 0.01% water by weight, less than 0.005% water by weight, less than 0.001% water by weight, or any other or intermediate value. This protective gas can form a protective curtain through which the cryogen can be dispensed to prevent the entrainment of ambient moisture in the cryogen. In some embodiments, for example, the entrainment of ambient moisture in the cryogen can adversely impact the temperature of the cryogen and/or the ability to control the temperature of the skin or the cryogen at the skin. Entrained moisture can be detrimental to the operation of the applicator 114 as entrained moisture can block one or several orifices 404 and prevent proper dispensing of cryogen. Further, entrained moisture can result in the creation of a "snow" layer on the skin from the accumulation of ice crystals formed from the entrained moisture. This layer of ice can insulate the skin and can prevent the providing of the desired treatment to the skin.

The protective gas can be dispensed from the same orifices 404 from which the cryogen is dispensed by delivering the protective gas before the delivery of the cryogen, or the protective gas can be delivered from separate orifices 404, such as curtain orifices 604, also referred to herein as curtain apertures 604 or curtain openings 604, than those from which the cryogen is dispensed. As used herein, a curtain orifice 604 refers to an orifice 404 through which the protective gas is delivered, and a cryogen orifice 606, also referred to herein as a cryogen aperture 606 or a cryogen opening 606, refers to an orifice 404 through which a cryogen is delivered. In some embodiments, a plurality of curtain orifices 604 can create an array of curtain orifices 604, and a plurality of cryogen orifices 606 can create an array of cryogen orifices 606.

In some embodiments, for example, one or more of the rows 602-A, 602-B, 602-C of orifices 404 can be selected for delivery of cryogen and one or more of the rows 602-A, 602-B, 602-C of orifices 404 can be selected for delivery of the protective gas. In one embodiment, for example, one or several of the orifices 404 and/or one or several of the rows 602-A, 602-B, 602-C of orifices 404 are selected for delivery of the protective gas simultaneously or partially simultaneously with the delivery of the cryogen. In one such embodiment, for example, some or all of the orifices 404 in one or both of the rows 602-A and 602-C can be curtain orifices 603 configured for delivery of protective gas simultaneously or partially simultaneously with the delivery of the cryogen from one or several cryogen orifices that can be located in the row 604-B. In some embodiments, curtain orifices 604 can be positioned to form a perimeter around the cryogen orifices 606. In such an embodiment, the orifices 404 in the rows 602-A and 602-C are curtain orifices 604 and additionally, the orifice 404 in row 602-B most proximate to a first end 806 of the nozzle tube 206 and the orifice 404 in row 602-B most proximate to a second end 808 of the nozzle tube 206 are curtain orifices.

In some embodiments, some or all of the orifices 404 can deliver a heated gas. In some embodiments, for example, the cryogen and the heated gas can be alternative delivered to cycle temperature of the skin of the patient. In some embodiments, the heated gas can be delivered through orifices 404 distinct from the orifices 404 through which cryogen is delivered, and in some embodiments, the heated gas can be delivered through the same orifices 404 through which cryogen is delivered.

The nozzle 116 can further include a shroud 700 that can shield one or several of the orifices 404. In some embodiments, for example, the shroud 700 can be sized and shaped to shield the plurality of orifices 404 from contact with moist air and/or from the formation of ice crystals that could obstruct one or several of the orifices 404. Specifically, in some embodiments, the shroud 700 can create a stagnation zone at the external and/or distal openings of the orifices. In some embodiments, the shroud 700 can comprise the same material as the nozzle tube 206, and in some embodiments, the shroud 700 can comprise a different material than the nozzle tube 706. In some embodiments, for example, the shroud can comprise a material having a lower thermal conductivity than the material of the nozzle tube 706, or specifically, in some embodiments, the nozzle tube 706 can comprise a metal such as, for example, a steel, stainless steel, nickel or a nickel alloy, aluminum, or brass, and the shroud 700 can comprise a polymer.

The shroud 700 can extend wholly or partially around the linear array 600 of orifices 404. In some embodiments, the shroud comprises a rectangular or ovular aperture 702 that extends around the linear array 600 of orifices 404. The aperture 702 can have a width 704, a depth, and a length 706. In some embodiments, the shroud 700 can have a depth of approximately: 1× the diameter of the orifices 404, 2× the diameter of the orifices 404, 3× the diameter of the orifices 404, 5× the diameter of the orifices 404, 10× the diameter of the orifices 404, between 1× and 10× the diameter of the orifices 404, between 1× and 4× the diameter of the orifices 404, or any other or intermediate depth.

Figure 8:
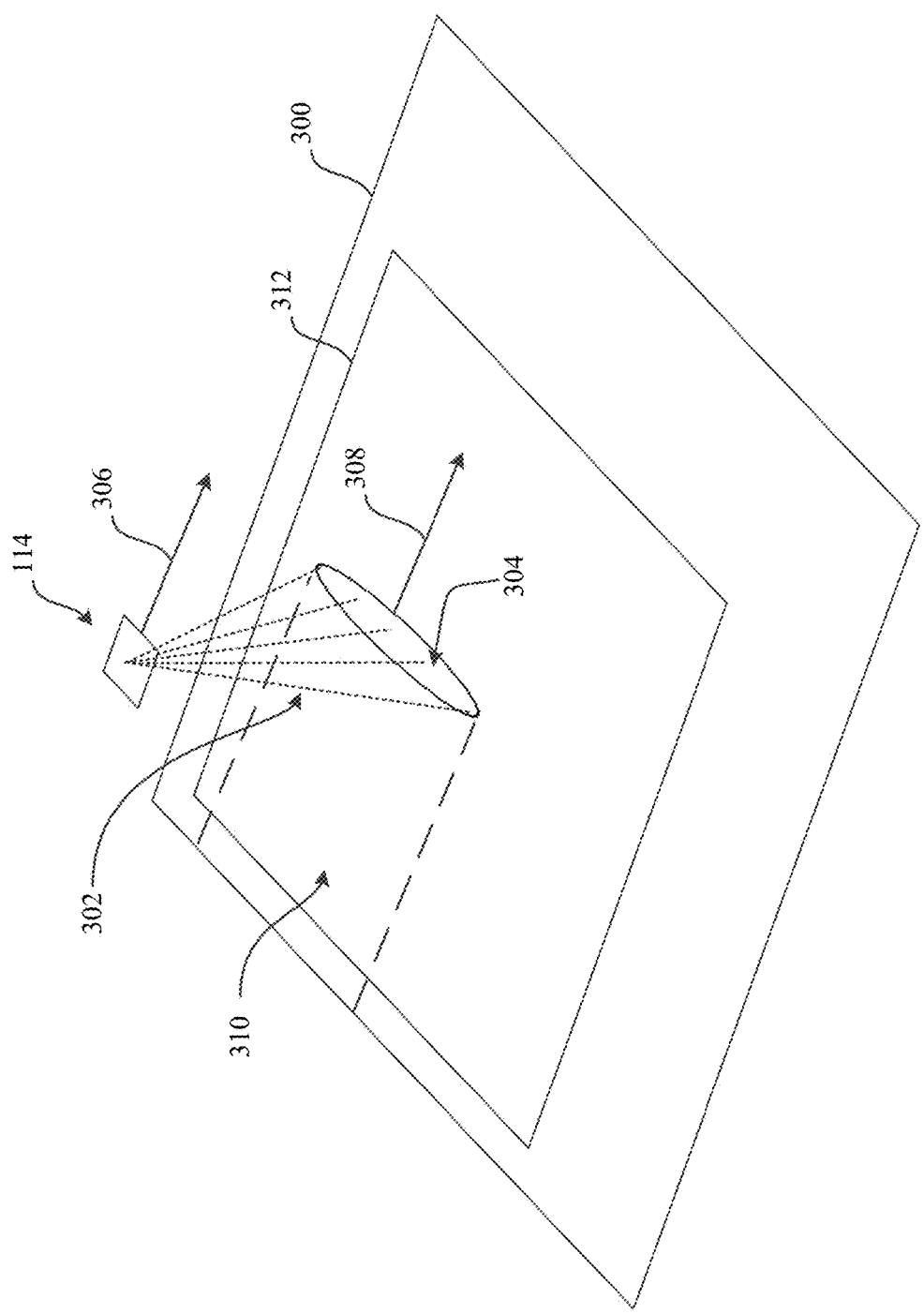
FIG. 8 is a schematic illustration of one embodiment of the application of cryogen to the skin of a patient.

FIG. 8 is a schematic illustration of one embodiment of the application of cryogen to the skin of a patient. As seen, the cryospray applicator 114 can be positioned at a location proximate to a portion of skin 300, also referred to herein as skin tissue 300, of the patient to be treated. The applicator 114 can be controlled to direct a planar spray 302, also referred to herein as a linear curtain, of cryogen, which can be or include liquid cryogen, or cold gas through the linear array 600 of orifices 404 in the nozzle 116 of the applicator 114. In some embodiments, the planar spray comprises a cryogen mist such as a liquid cryogen mist, and in some embodiments, the liquid cryogen can comprise liquid carbon dioxide. This liquid cryogen or cold gas can cool an area 304 of skin tissue 300 of the patient in a line of cooling treatment to effect a treatment of the skin 300. In some embodiments, the planar spray 302 can have a temperature at the skin surface of between −4° C. and −80° C.

The applicator 114 can be moved as indicated by arrow 306 in the direction indicated by arrow 306 which can result in the movement of the area 304 as indicated by arrow 308 in the direction indicated by arrow 308. This movement of the area 304 across the skin 300 of the patient can create a treated area 310 that can be continuous when the applicator 114 delivers a continuous planar spray 302 or interrupted when the applicator 114 delivers a non-continuous planar spray 302 such as by, for example, intermittently delivering the planar spray 302.

In some embodiments, a mask 312 can be applied to and/or overlaid upon the skin prior to delivery of the cryogen. This mask 312 can comprise an object, item, or substance. In some embodiments, the mask 312 can comprise a perforated member, a perforated film, a mesh, and/or a temperature controlled member. In some embodiments, for example, the temperature of the mask 312 can be controlled to control a temperature of all or portions of the skin, and specifically, in some embodiments, the mask 312 can be heated to heat the skin and/or to cyclically heat the skin. In some embodiments, the mask 312 can affect the temperature of the skin 300 by insulating and/or shielding the skin 300 from some of the cryogen applied to the skin 300 and/or to the mask 312 by the applicator 114.

Figure 9:
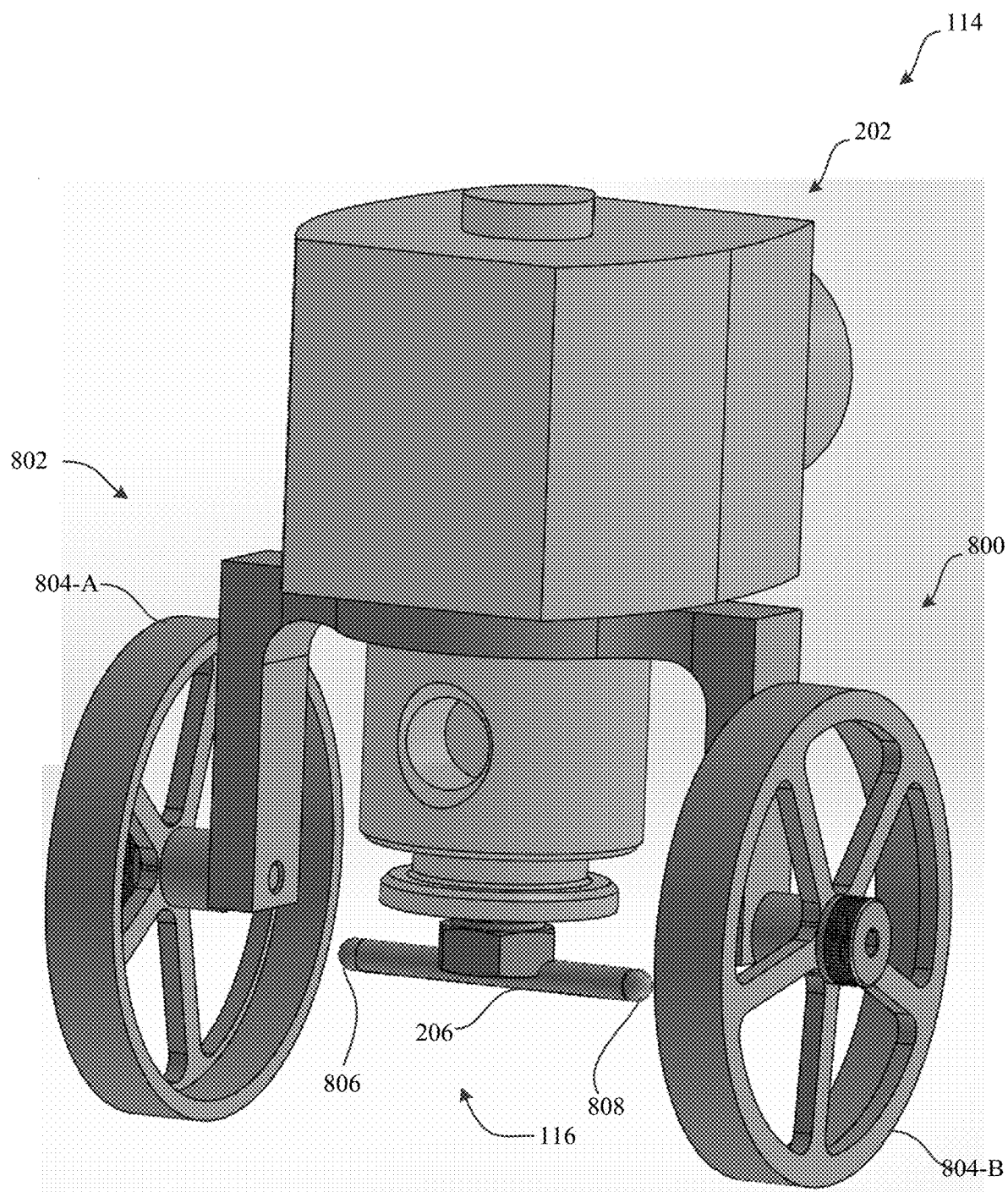
FIG. 9 is a perspective view of one embodiment of a wheeled spacer.
Figure 10:
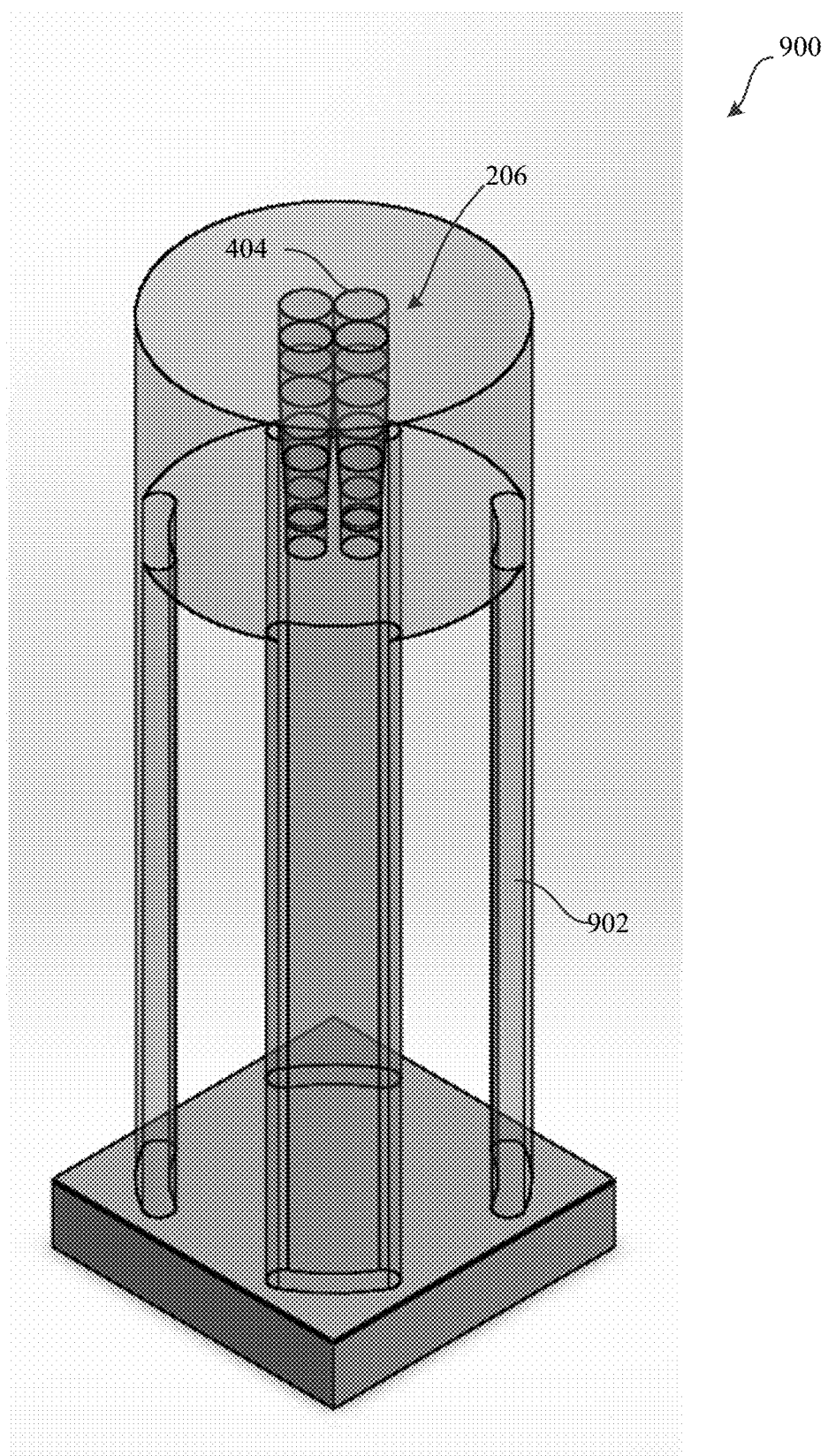
FIG. 10 is a perspective view of one embodiment of a slider spacer.

In some embodiments, the applicator 114 can further include a spacer, and specifically a mechanical spacer 800 as shown in FIGS. 9 and 10. The mechanical spacer 800 can be configured to engage with the skin of the patient so as to maintain and/or at least maintain a desired, constant, and/or minimum spacing and/or distance between the nozzle 116 and/or orifices 404 or linear array 600 and the skin of the patient. The mechanical spacer 800 can be coupled to the head portion 202 and/or to the nozzle 116. The mechanical spacer 800 can comprise a variety of shapes, sizes, and designs. In some embodiments, the mechanical spacer 800 can maintain a fixed spacing between the skin of the patient and the nozzle 116 and/or orifices 404 or linear array 600, and in some embodiments, the mechanical spacer 800 can be adjustable to change the desired, constant, and/or minimum spacing and/or distance.

The mechanical spacer 800 can comprise a wheeled spacer 802. The wheeled spacer 800 can include one or several wheels 804 including, for example, 1, 2, 3, 4, 6, 8, 10, or any other or intermediate number of wheels 804. In the embodiment of FIG. 8, the wheeled spacer 802 includes a first wheel 804-A and a second wheel 8004-B. The first wheel 804-A is located proximate to the first end 806 of the nozzle tube 206 and/or of the linear array 600, and the second wheel 804-B is located proximate to the second end 808 of the nozzle tube 206 and/or of the linear array 600.

The mechanical spacer 800 can comprise a slider spacer 900. The slider spacer 900 can include a plurality of legs 902 or prongs 902 including, for example, 1, 2, 3, 4, 6, 8, 10, or any other or intermediate number of legs 902. In some embodiments, the legs 902 can be adjustable with respect to the nozzle 116 and/or the linear array 600 of orifices 404 to change the distance between the nozzle 116 and/or the linear array 600 of orifices 404 and the patient's skin.

Figure 11:
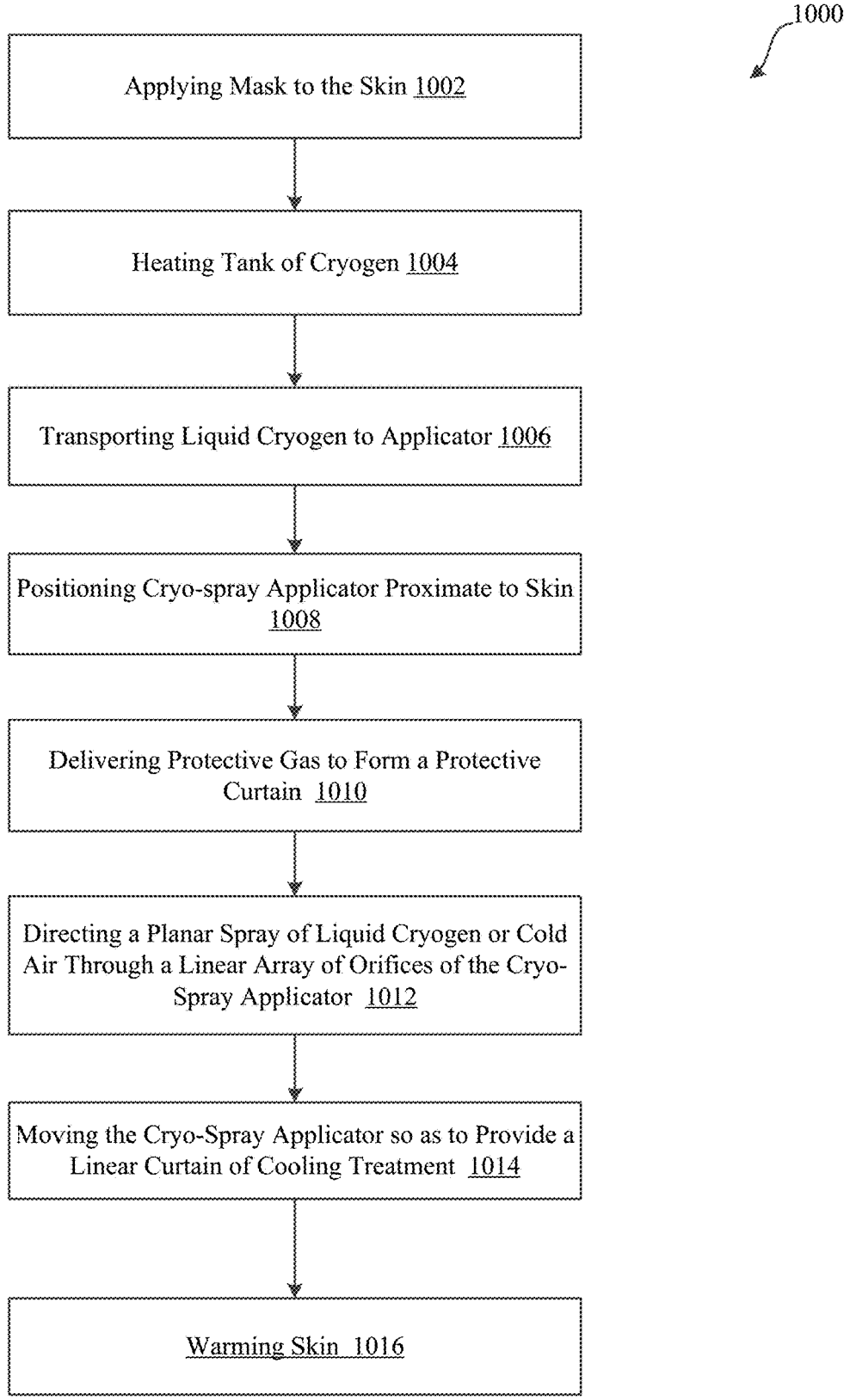
FIG. 11 is a flowchart illustrating one embodiment of a process for cooling skin of a patient by applying a cryogen spray.

With reference now to FIG. 11, a flowchart illustrating one embodiment of a process 1000 for cooling skin of a patient and/or for applying the cryogen is shown. In some embodiments, the skin can be cooled and/or the cryogen can be applied as part of a cryogenic treatment. In some embodiments, this treatment can alter a pigmentation appearance and/or pigmentation of the treated skin, and in some embodiments, this treatment can alter a texture, tension, tone, smoothness, or tightness of the treated skin. In some embodiments, this cryogenic treatment can be to treat one or several indications that can affect large areas of skin such as, for example: pigmentation or coloration related indications including hypopigmentation or hyperpigmentation; acne; rosacea; psoriasis or the like. In some embodiments, this cryogenic treatment can be to treat blemishes including pigmentation related blemishes. Such blemishes may include: melasma; lentigo; freckle; birthmark, liver spot, age spot, or café au lait macule.

The process can be performed with all or portions of the cryogenic treatment system 100. The process 1000 begins at block 1002, wherein the mask 312 is applied to the skin and/or placed on the skin. After the mask is applied to the skin, the cryogen supply 102 is heated as indicated by block 1004 of process 1000. In some embodiments, the mask can be applied to the skin prior to directing the planar spray from the linear array 600 of orifices 404. The cryogen supply 102 can contain cryogen that can be, for example, in both a liquid and a gaseous form. In some embodiments, the tank 102 can be heated by the heater 104 as controlled by the controller 108 according to information received from the thermostat 106. In some embodiments, the tank 102 can be heated to a desired temperature and/or until a desired pressure inside the tank 102 is reached. The tank 102 can be heated, in some embodiments, such that the tank 102 maintains the desired pressure.

After the tank is heated, the cryogen, and specifically liquid cryogen is transported from the cryogen supply 102 to the applicator 114 via the supply tube 118 as indicated in block 1006 of process 1000. In some embodiments, the cryogen can be transported through the tube 118 via a pressure differential that can arise, for example, from the opening of the valve 218. In some embodiments, the pressure of the liquid cryogen in the tube 118 can be equal and/or approximately equal to the pressure of the liquid cryogen in the tank 102.

At block 1008 of process 1000, the applicator 114 is positioned proximate to the skin of the patient. In some embodiments, positioning the cryospray applicator 114 proximate to the skin of the patient, and particularly to the area of the skin tissue of the patient to be treated can include positioning a non-contact cryospray applicator 114 proximate to the area of the skin tissue of the patient, or positioning a cryospray applicator 114 including a mechanical spacer 800 proximate to the area of the skin tissue of the patient. In some embodiments, this can include positioning the applicator a desired distance from the skin of the patient, which can include, for example, adjusting the mechanical spacer 800 so that the applicator 114 is maintained at the desired distance from the skin of the patient by the mechanical spacer 800. The mechanical spacer 800 can, in some embodiments, comprise the wheeled spacer 802 and/or the sliding spacer 900. In some embodiments, and as part of positioning the applicator 114, the skin of the patient can be contacted with the mechanical spacer 800. In some embodiments, the mechanical spacer can maintain the predetermined distance between the applicator 114 and the skin. In some embodiments, this predetermined distance can be, for example, between 1 inch and 3 inches, and/or between 0.125 inches and 3 inches.

At block 1010, the protective gas is delivered to form a protective curtain. In some embodiments, the creation of a protective curtain can include the dispensing of protective gas that can include an inert gas and/or a dry gas. In some embodiments, the protective gas can be delivered before, during, and/or after delivery of the cryogen. The protective gas can be delivered from the same orifices 404 from which the cryogen is delivered, or from different orifices 404, such as one or several curtain orifices 604, than the orifices 404 from which the cryogen is delivered. In some embodiments, this protective curtain can prevent water entrainment or ambient air entrainment as the cryogen, which can include: a liquid cryogen; a gaseous cryogen; a two-phase fluid; cooled air; and/or carbon dioxide and/or cold gas moves downstream of the orifices 404 as delivery of the cryogen from the orifices 404.

At block 1012, the cryogen is dispensed, delivered, and/or expelled from the applicator 114, and specifically, a planar spray 302 of cryogen or cold gas is directed through the linear array 600 of orifices 404 of the cryospray applicator 114. In some embodiments, this can include the control of the applicator 114 to dispense and/or expel the cryogen. In some embodiments this can include, for example, the manipulation of the control feature 220 to cause the dispensing and/or expelling of the cryogen from the applicator 114. In some embodiments, the cryogen can be dispensed and/or expelled from the nozzle 206, and particularly from the linear array of orifices 600 to form a linear curtain of cryogen downstream from the nozzle 206.

In some embodiments, directing the planar spray of cryogen or cold gas through the linear array of orifices can include locally freezing an epidermis. This local freezing of the epidermis can alter a pigmentation of the area of the skin tissue of the patient. In some embodiments, directing the planar spray of cryogen or cold gas through the linear array of orifices can include locally disrupting an epidermis. This local disruption of the epidermis can result in the gradual skin lightening in the area of the skin tissue of the patient.

In some embodiments, the step of block 1012 can include transporting cryogen from the cryogen supply 102 to the applicator 114 via the supply tube 118, and in other embodiments, this can be a separate step as indicated in FIG. 11. In some embodiments, a pressure of the cryogen at the supply tube 118 can be substantially equal to the desired pressure in the cryogen supply 102.

At block 1014, the cryospray applicator 114 can be moved with respect to the skin as indicated, for example, in FIG. 8. In some embodiments, the movement of the applicator 114 can provide a linear curtain of cooling treatment to the skin, and specifically to the area 304 of skin tissue 300 of the patient. In some embodiments, the applicator 114 can be moved by hand, and in other embodiments, the applicator 114 can be moved by a machine.

After the cryospray applicator 114 has been moved, the process 1000 can proceed to block 1016, wherein all or portions of the skin are warmed. In some embodiments, this warming can be performed via the mask 312, and in some embodiments, this warming can be performed via the applicator 114. In one embodiment, for example, a warm gas, cryogen, and/or air can be dispensed by the nozzle 116 to the skin to warm the skin, and specifically to convectively warm the skin. In some embodiments, the warm gas, cryogen, and/or air can be dispensed by the same or different orifices 404 as dispense the protective gas and/or the cryogen.

In some embodiments some or all of the steps of process 1000 can be repeated in the course of a single treatment. In some embodiments, for example, some or all of the steps of blocks 1010 through 1016 can be repeated one or several times as part of a treatment. This can include, for example, the repeated directing of the planar spray and/or the delivering of the cryogen or cold gas, the moving of the applicator, and the warming of the skin. In some embodiments, this cyclical warming and cooling of the skin may provide treatment benefits and this cycle can be performed to maximize these treatment benefits and/or to achieve a desired treatment benefit.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of cooling an area of skin tissue of a patient, the method comprising:
positioning a cryospray applicator to a position proximate to the area of skin tissue of the patient to be treated;
directing a planar spray of cryogen through a linear array of orifices of the cryospray applicator to cool the area of skin tissue of the patient in a line of cooling treatment to effect a treatment of the area of skin tissue; and
moving the cryospray applicator non-parallel to the line of cooling treatment while directing the planar spray of cryogen to provide a moving linear curtain of cooling treatment to cool the area of skin tissue of the patient and create a continuous treated area.

2. The method of claim 1, further comprising: detecting an attribute of cryogen within a tank; and controlling a heater to heat the tank such that the tank maintains a desired pressure.

3. The method of claim 2, wherein directing the planar spray of cryogen through the linear array of orifices comprises transporting liquid cryogen from the tank to the cryospray applicator via a supply tube, wherein a pressure of the liquid cryogen in the supply tube is substantially equal to a desired pressure in the tank.

4. The method of claim 3, wherein directing the planar spray of cryogen through the linear array of orifices comprises transporting liquid cryogen through the cryospray applicator to an internal volume of a nozzle tube.

5. The method of claim 4, wherein the nozzle tube comprises centrally located nozzle base defining a channel fluidly connecting the supply tube to the internal volume of the nozzle tube, and wherein the nozzle tube comprises an elongate member defining the orifices in the linear array of orifices, the orifices extending into the internal volume of the nozzle tube.

6. The method of claim 5, wherein a shroud extends around the orifices, and wherein the shroud creates a stagnation zone surrounding the orifices during directing of the planar spray of cryogen through the linear array of orifices of the cryospray applicator.

7. The method of claim 1, wherein the cryogen comprises: a liquid cryogen; a gaseous cryogen; a two-phase fluid; cooled air; or carbon dioxide.

8. The method of claim 7, wherein the liquid cryogen comprises liquid carbon dioxide.

9. The method of claim 1, wherein the cryogen comprises a plurality of droplets.

10. The method of claim 1, wherein the planar spray of cryogen has a temperature at a surface of the area of skin tissue of between −4 C to −80 C.

11. The method of claim 1, wherein each orifice comprises a cylindrical opening.

12. The method of claim 1, wherein the linear array of orifices comprises a single row of orifices or a plurality of rows of orifices.

13. The method of claim 1, further comprising delivering a gas to form a protective curtain through which the cryogen moves downstream of the orifices.

14. The method of claim 13, wherein the protective curtain prevents water entrainment or ambient air entrainment as the cryogen moves downstream of the orifices.

15. The method of claim 13, wherein the gas is expelled from the orifices before or during the directing the planar spray of cryogen from the orifices.

16. The method of claim 13, wherein the gas comprises at least one of: a dry gas; and an inert gas.

17. The method of claim 1, further comprising applying a mask to the area of skin tissue of the patient prior to directing the planar spray of cryogen from the linear array of orifices.

18. The method of claim 17, wherein the mask comprises a perforated film.

19. The method of claim 1, wherein positioning the cryospray applicator to the position proximate to the area of skin tissue of the patient to be treated comprises contacting the area of skin tissue of the patient with a mechanical spacer to maintain a predetermined distance between the cryospray applicator and the area of skin tissue.

20. The method of claim 19, wherein the predetermined distance comprises a range from 0.125 inches to 3 inches.

21. The method of claim 19, wherein the mechanical spacer comprises at least one of: a wheeled spacer; and a sliding spacer.

22. The method of claim 1, wherein positioning the cryospray applicator to the position proximate to the area of skin tissue of the patient to be treated comprises positioning a non-contact cryospray applicator proximate to the area of skin tissue of the patient.

23. The method of claim 1, further comprising warming the area of skin tissue of the patient after the cooling treatment.

24. The method of claim 23, wherein the area of skin tissue of the patient is warmed by delivery of warm air from the same or different orifices for convective warming.

* * * * *